US011241457B2

(12) United States Patent
Ahn et al.

(10) Patent No.: US 11,241,457 B2
(45) Date of Patent: Feb. 8, 2022

(54) COMPOSITION COMPRISING RED CELL-DERIVED MICROPARTICLES AND METHOD OF TREATING EXCESSIVE BLEEDING

(71) Applicant: RxMP Therapeutics, Inc., Miami, FL (US)

(72) Inventors: Yeon S. Ahn, Pinecrest, FL (US); Wenche Jy, Miami, FL (US); Lawrence L. Horstman, Plantation, FL (US); Rifat Pamukcu, Philadelphia, PA (US)

(73) Assignee: RxMP Therapeutics, Inc., Miami, FL (US)

( * ) Notice: Subject to any disclaimer, the term of this patent is extended or adjusted under 35 U.S.C. 154(b) by 146 days.

(21) Appl. No.: 16/465,054

(22) PCT Filed: Nov. 29, 2017

(86) PCT No.: PCT/US2017/063700
§ 371 (c)(1),
(2) Date: May 29, 2019

(87) PCT Pub. No.: WO2018/102409
PCT Pub. Date: Jun. 7, 2018

(65) Prior Publication Data
US 2019/0321406 A1 Oct. 24, 2019

Related U.S. Application Data

(60) Provisional application No. 62/428,155, filed on Nov. 30, 2016.

(51) Int. Cl.
*A61K 35/18* (2015.01)
*A61P 7/04* (2006.01)
*A61K 9/00* (2006.01)
*A61K 9/14* (2006.01)

(52) U.S. Cl.
CPC ............ *A61K 35/18* (2013.01); *A61K 9/0019* (2013.01); *A61K 9/14* (2013.01); *A61P 7/04* (2018.01)

(58) Field of Classification Search
None
See application file for complete search history.

(56) References Cited

U.S. PATENT DOCUMENTS

| 4,529,561 | A | 7/1985 | Hunt et al. |
| 5,332,578 | A | 7/1994 | Chao |
| 5,690,963 | A | 11/1997 | Spargo et al. |
| 7,811,558 | B2 | 10/2010 | Ho et al. |
| 8,105,632 | B2* | 1/2012 | Jy ................ A61P 7/00 424/533 |
| 9,155,764 | B1* | 10/2015 | Ahn ................ A61K 35/18 |
| 2003/0040480 | A1 | 2/2003 | Rojkjaer | |

| 2008/0057505 | A1 | 3/2008 | Lin et al. |
| 2008/0069807 | A1 | 3/2008 | Jy et al. |
| 2013/0316011 | A1 | 11/2013 | Ahn et al. |
| 2016/0263156 | A1 | 9/2016 | Lee et al. |
| 2017/0080027 | A1* | 3/2017 | Ahn ................ A01N 1/0284 |

FOREIGN PATENT DOCUMENTS

| JP | 2008-522974 A | 7/2008 |
| WO | 2000/29029 A1 | 5/2000 |
| WO | 2006/062945 A2 | 6/2006 |
| WO | 2016/141325 A1 | 9/2016 |

OTHER PUBLICATIONS

Westerman M. et al. Red Blood Cell Derived Microparticles: An Overview Blood Cells, Molecules and Diseases 59:134-139, 2016. (Year: 2016).*
Horstman L. et al. Elevated Cholinesterase Activity in Patients with TIA and Other Thrombotic Disorders. Blood 114(22)1167, Nov. 2009. (Year: 2009).*
Bidot, C. et al. Plasma Cholinesterase Activity in ITP Patients With/Without Thrombosis. Blood 114(22)1536 Nov. 2009 (Year: 2009).*
Ahn et al., Red cell derived microparticles (RMP) as hemostatic agent to treat bleeding disorders: The mode of action of RMP, Presented at the International Society of Thrombosis & Hemostasis, JTH (Suppl. 2): 269(2011).
Ahn, Cell-derived microparticles: miniature envoys with many faces, J. Thrombosis and Haemostasis, 3:884-887 (2005).
Ahn, Red cell microparticles (RMP) as hemostatic agent: summary of recent advance', American Society of Hematology, 53rd ASH Annual Meeting and Exposition, 2260 (2011).
Bevers et al., Defective Ca2+-induced microvesiculation and deficient expression of procoagulant activity in erythrocytes from a patient with a bleeding disorder: a study of the red blood cells of Scott syndrome, Blood, 79:380-388 (1992).
Bidot et al., Microparticle-mediated thrombin generation assay: increased activity in patients with recurrent thrombosis, J. Thromb Haemost, 6:913-919 (2007).
Biro et al., Human cell-derived microparticles promote thrombus formation In vivo in a tissue factor-dependent manner, J. Thrombosis and Haemostasis, 1(12):2561-2568 (2003).
Blajchman, Novel platelet products, substitutes and alternatives, Transfus. Clin. Biol., 8:267-271 (2001).
Bode et al., Vesiculation of platelets during in vitro aging, Blood, 77:887-895 (1991).
Butikofer et al., Modulation of erythrocyte vesiculation by amphiphilic drugs, Biochimica et Biophysica Acta., 901(2):291-5 (1987) (Abstract Only).
Camus et al., Erythrocyte microparticles can induce kidney vasoocclusions in a murine model of sickle cell disease, Blood, 120:5050-5058 (2012).

(Continued)

*Primary Examiner* — Ralph J Gitomer
(74) *Attorney, Agent, or Firm* — Marshall, Gerstein & Borun LLP

(57) ABSTRACT

The disclosure provides a composition comprising red cell-derived microparticles (RMPs) demonstrating acetylcholine esterase (AchE) activity of less than 350 pmol/min/$10^6$ particles/uL. The disclosure further provides a method of treating excessive bleeding comprising administering the composition to a subject.

16 Claims, 4 Drawing Sheets

(56) References Cited

OTHER PUBLICATIONS

Casals et al., Physical stability of liposomes bearing hemostatic activity, Chem. Phys. Lip., 125:139-146 (2003).
Combes et al., In Vitro Generation of Endothelial Microparticles and Possible Prothrombotic Activity in Patients With Lupus Anticoagulant, J. Clin. Investigation, 104(1):93-102 (1999).
Danesh et al., Exosomes from red blood cell units bind to monocytes and induce proinflammatory cytokines, boosting T-cell responses in vitro, Blood, 123:687-696 (2014).
Davis et al., Thromboelastography for the prediction of bleeding after transplant renal biopsy, J. Am. Soc. Neph., 6(4):1250-5 (1995).
Diaz et al., Generation of phenotypically aged phosphatidylserine-expressing erythrocytes by dilauroyphosphatidylcholine-induced vesiculation, Blood, 87:295-2961 (1996).
Donadee et al., Nitric oxide scavenging by red blood cell microparticles and cell-free hemoglobin as a mechanism for the red cell storage lesion, Circulation, 124:465-476 (2011).
Ellman et al., A new and rapid colorimetric determination of acetylcholinesterase activity, Biochemical Pharmacology, 7:88-95 (1961).
Foster et al., Lipid raft proteomics: more than just detergent-resistant membranes, Subcell Biochem., 43:35-47 (2007).
Galan et al., Possible hemostatic effect of synthetic liposomes in experimental studies under flow conditions, Hematologic, 87:615-23 (2002).
Galli et al., Platelet-derived microvesicles in thrombotic thrombocytopenic purpura and hemolytic uremic syndrome, Thromb. Haemost., 75:427-31 (1996).
George et al., Isolation of human platelet membrane microparticles from plasma and serum, Blood, 60:4 (1982).
Gladwin et al., Hemolysis and cell-free hemoglobin drive an intrinsic mechanism for human disease, J. Clin. Invest., 122:1205-1208 (2012).
Hagerstrand et al., Vesiculation Induced by Amphiphiles in Erythrocytes, Biochem. Biophys. Acta., 982:179-186 (1989).
Hamilton et al., Unilamellar liposomes made with the french pressure cell: A simple preparative and semiquantitative technique, J. Lipid. Res., 21:981-992 (1980).
Hannon et al., The contemporary economics of transfusions. In Perioperative Transfusion Medicine; Speiss RD, Spence RK, Shander A (eds.), Lippincott Williams and Wilkins, 13 (2006).
Harris et al., Physical properties of erythrocyte ghosts that determine susceptibility to secretory phospholipase A2, J. Biol. Chem., 276(25):22722-22731 (2001).
Hawskworth et al: Evaluation of lyophilized platelets as an infusible hemostatic agent in experimental non non-compressible hemorrhage in swine. J. Thromb Haemost., 7(10):1663-71 (2009).
Hedner, NovoSeven as a universal hemostatic agent. Blood Coagul Fribrinolysis, 11(Suppl 1):S107-11 (2000).
Hemker, Calibrated automated thrombin generation measurement in clotting plasma, Pathophysiol Haemost Thromb, 33(1):4-15 (2003).
International Application No. PCT/US17/63700, International Search Report and Written Opinion, dated Feb. 2, 2018.
International Application No. PCT/US2005/044064, International Preliminary Report on Patentability, dated Jun. 13, 2007.
International Application No. PCT/US2005/044064, International Search Report and Written Opinion, dated Aug. 31, 2006.
International Application No. PCT/US2012/023020, International Preliminary Report on Patentability, dated Aug. 8, 2013.
International Application No. PCT/US2012/023020, International Search Report and Written Opinion, dated Aug. 14, 2012.
Jimenez et al., Activation-derived endothelial microparticles (EMP) are elevated in thrombotic thrombocytopenia pupura (TTP): detection of von willebrand factor (vWF)-positive EMP during the acute phase of TTP in vitro and in vivo, Abstract No. 40, 44th Annual meeting of the American Society of Hematology, Blood, 100 (2002).
Jimenez et al., Endothelial cells release phenotypically and quantitatively distinct microparticles in activation and apoptosis, Thrombosis Research, 109:175-180 (2003).
Jy et al, Microparticles in stored red blood cells as potential mediators of transfusion complications, Transfusion, 51(4):886-93 (2011).
Jy et al., Red cell-derived microparticles (RMP) as haemostatic agent, Thromb Haemost, 110:751-760 (2013).
Jy et al., Thrombin generation profiles are qualitatively and quantitatively distinct in microparticles derived from red cells (RMP), platelets (PMP), and endothelia (EMP), Blood, 108(11):499a (2006) (Ab1759).
Koopman et al., Annexin V for flow cytometric detection of phosphatidylserine expression on B cells undergoing apoptosis, Blood, 84:1415-1420 (1994).
Lacroix et al., Revisited role of microparticles in arterial and venous thrombosis, J. Throm. Haemost., 11(Suppl.1):24-35 (2013).
Lelkes et al., Interaction of french-pressed liposomes with isolated bovine adrenal chromaffin cells, J. Biol. Chem., 260(3):1796-1803 (1985).
Levi et al., Fibrinogen-coted albumin microcapsules reduce bleeding in severely thrombocytopenic rabbits, Nat. Med., 5(1):107-111 (1999).
Lew et al., Mechanism of spontaneous inside-out vesiculation of red cell membranes, J. Cell. Biol., 106:1893-1901 (1988).
Luddington et al., Clinical measurement of thrombin generation by calibrated automated thrombography requires contact factor inhibition, J. Thromb Haemost, 2(11):1954-1959 (2004).
Mallat et al., Elevated levels of shed membrane microparticle with procoagulant potential in the peripheral circulating blood of patients with acute coronary syndromes, Circulation, 101:841-843 (2000).
Mannucci, Desmopressin (DDAVP) in the treatment of bleeding disorders: the first 20 years, Blood, 90(7):2515-21 (1997).
Mcgill et al., Platelet membrane vesicles reduced microvascular bleeding times in thrombocytopenic rabbits, J. Laboratory and Clin. Med., 109(2):127-133 (1987).
Miyazaki et al, High shear stress can initiate both platelet aggregation and shedding of procoagulant containing microparticles, Blood, 88: 3456-3464, (1996).
Nomura et al., High-shear-stress-induced activation of platelets and microparticles enhances expression of cell adhesion molecules in THP-1 and endothelial cells, Atherosclerosis, 158:277-287 (2001).
Office Action in Japanese Patent Application No. 2013-551393, dated Sep. 30, 2014.
Okamura et al., Hemostatic effects of phospholipid vesicles carrying fibrinogen gamma-chain dodecapeptide in vitro and in vivo, Bioconjugate Chem., 16:1589-1596 (2005).
Owens et al., Microparticles in hemostasis and thrombosis, Circ. Res., 108:1284-1297 (2011).
Parnham, Toxicity screening of liposomes, Chem. Phys. Lipids., 64:263-74 (1993).
Piacibello et al., Ex vivo expansion of megakaryocytes, Transfusion Science, 22:107-110 (2000).
Piccin et al., Circulating microparticles: Pathophysiology and clinical implications, Blood Rev., 21:157-171 (2007).
Plotkin et al., A reduction in clot formation rate and strength assessed by thromboelastography is indicative of transfusion requirements in patients with penetrating injuries, J. Trauma, 64(2 Suppl.): S64-8 (2008).
Ratajczak et al., Membrane-derived microvesicles: Important and underappreciated mediators of Cell-To-Cell communication, Leukemia, 20:1487-1495 (2006).
Ronald et al., Can the use of thromboelastography predict and decrease bleeding and blood and blood product requirements in adult patients undergoing cardiac surgery?, Interact CardioVas Thorac. Surg., 4:456-63 (2005).
Rubin, Erythrocytes Microparticles, Thesis, Universite de Geneve (2007).
Rybak et al., A liposome based platelet substitute, the plateletsome, with hemostatic efficacy, Biomat. Art. Cells Immob. Biotech., 21(2):101-118 (1993).
Salzer et al., Vesicles generated during storage of red cells are rich in the lipid raft marker stomatin, Transfusion, 48:451-462 (2008).

(56) References Cited

OTHER PUBLICATIONS

Schrier et al., Physical Characteristics of Nonimmunologic Adherence of IgG to RBC Ghost Membranes, Clin. Exp. Immunol., 11:235-244 (1972).
Solheim et al., Rational use of blood products, European Journal of Cancer, 37:2421-2427 (2001).
Taylor et al., Infusion of phospholipid vesicles amplifies the local thrombosis to TNF and anti-protein C into a consumptive response, Thromb Haemost, 75:574-84 (1996).
Toissel, ASHP Handbook on Injectable Drugs, 4th ed., 622-630 (1986).
Warkenton, An overview of the heparin-Induced thrombocytopenia syndrome, Seminars in thrombosis and homeostasis, 30(3) (2004).
Wenche et al., Clinical significance of platelet microparticles in autoimmune thrombocytopenias, J. Laboratory and Clin. Med., 119(4):334-345 (1992).
Whitlow et al., Cells lacking glycan phosphatidylinositol-linked proteins have impaired ability to vesiculate, Blood, 81:510-516 (1993).
Willekens et al., Erythrocyte vesiculation: A self-protective mechanism?, Brit. J. Haem., 141:549-556 (2008).
Wolf, The nature and significance of platelet products in human plasma, Brit. J. Haemat, 13:269-288 (1967).
Wolkmer et al., Biochemistry detection of acetylcholinesterase activity in Trypanosoma evansi and possible functional correlations, Experimental Parasitology, 132:546-549 (2014).
Xie at al., Targeting acetylcholinesterase to membrane rafts: a function mediated by the proline-rich membrane anchor (PRiMA) in neurons, J. Biol. Chem., 285:11537-11546 (2010).
Xie et al., Regulation of a transcript encoding the proline-rich membrane anchor of globular muscle acetylcholinesterase. The suppressive roles of myogenesis and innervating nerves, J. Biol. Chem., 282:11765-11775 (2007).
Yamaguchi et al., Effects of temperature and pH on hemoglobin release from hydrostatic pressure-treated erythrocytes, J. Biohem., 106:1080-1085 (1989).
Yamaguchi et al., Vesiculation induced by hydrostatic pressure in human erythrocytes, J. Biochem., 110:355-359 (1991).
Zwicker et al., Prediction and prevention of thromboembolic events with enoxaparin in cancer patients with elevated tissue factor-bearing microparticles: a randomized-controlled phase II trial (the Microtec study), Br. J. Haematol., 160:530-537 (2013).
Cho et al., Functional heterogeneity of red cell-derived microparticles from different sources: calcium ionophore vs. storage vs. extrusion, Blood, 128:3770.

\* cited by examiner

COMPOSITION COMPRISING RED CELL-DERIVED MICROPARTICLES AND METHOD OF TREATING EXCESSIVE BLEEDING

CROSS REFERENCE TO RELATED APPLICATION

This application claims priority to U.S. Provisional Patent Application No. 62/428,155, filed Nov. 30, 2016, which is hereby incorporated by reference in its entirety.

TECHNICAL FIELD OF THE INVENTION

The disclosure is related to a composition comprising red cell-derived microparticles (RMPs) and methods of use.

BACKGROUND

Excessive bleeding is among the most common of life-threatening complications in trauma and bleeding complications. Blood transfusions are the mainstay for treating excessive blood loss. Therapies targeting the underlying causes of bleeding disorders differ depending on etiology. Platelet transfusion or interventions that raise platelet count are employed to arrest bleeding due to low platelet counts (thrombocytopenia). In the case of coagulation disorders, blood factor replacement is typically administered. In hemophilia A, Factor VIII is administered to a subject, whereas hemophilia B calls for Factor IX treatment.

Existing therapies suffer from significant drawbacks. For example, donated blood for transfusions is becoming increasingly scarce and expensive due to rising demand, limited supply, and more stringent regulations. According to the American Red Cross, approximately 36,000 units of red blood cells are needed every day in the U.S. alone. See www.redcrossblood.org/learn-about-blood/blood-facts-and-statistics. The hospital cost for transfusion-related adverse effects exceeds $10 billion per year. Hannon & Gjerde: The contemporary economics of transfusions. In Perioperative Transfusion Medicine; Speiss R D, Spence R K, Shander A (eds.), Lippincott Williams and Wilkins, p. 13 (2006). Transfusions also are associated with many short- and long-term complications including anaphylaxis, hemolytic reactions, transfusion induced immune suppression, graft-versus host disease, and transfusion-related acute lung injury (TRALI). Platelet MP (PMP) and lyophilized whole platelets (LyoPLT) have disadvantages such as, e.g., high cost, scarcity of platelets, risk of thrombogenesis, and immunoreactivity. Platelets are highly immunogenic due to HLA, ABO, Rh, and platelet-specific antigens, which are impractical to cross match, hence adverse reactions are frequent. Furthermore, platelets are known to carry tissue factor (TF) which is thrombogenic.

There remains a need in the art for agents that can be administered safely and immediately after detection of excessive bleeding, and at reasonable cost.

SUMMARY OF THE INVENTION

The disclosure provides a composition comprising red cell-derived microparticles (RMPs) demonstrating acetylcholine esterase (AchE) activity of less than 350 pmol/min/$10^6$ particles (e.g., less than 200 pmol/min/$10^6$ particles). In various aspects, 20%-50% of the RMPs in the composition display phosphatidylserine. Optionally, the composition shortens time to initial clot formation as measured by thromboelastography (TEG) in whole blood and plasma, for example, by at least two minutes. Also optionally, the mean diameter of the RMPs is about 0.40-0.6 µm. Further provided is a method for treating excessive bleeding in the subject, the method comprising administering to the subject the RMP composition described herein.

DETAILED DESCRIPTION OF THE INVENTION

Figure 1:
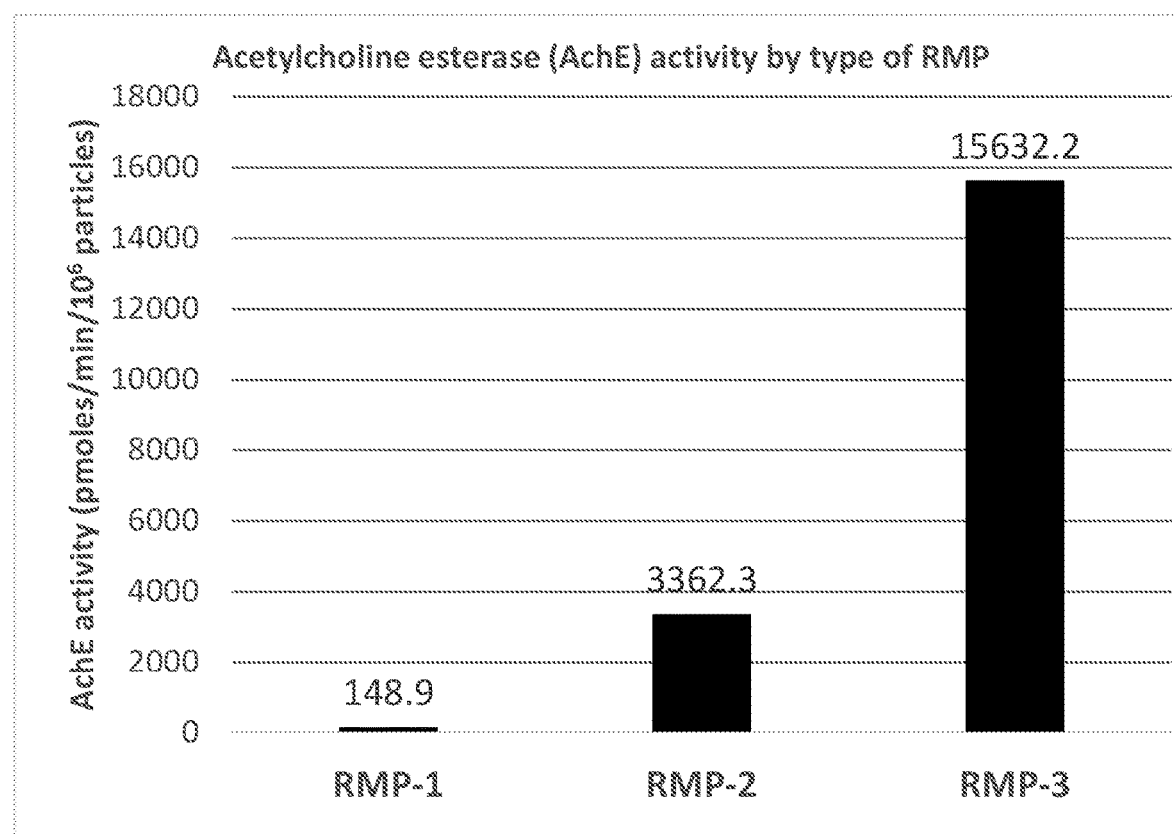
FIG. 1 is a bar graph comparing acetylcholinesterase (AChE) activity (µM/min/$10^6$ RMP; y-axis) expressed in RMP-1, RMP-2, and RMP-3 described in the Examples.
Figure 2:
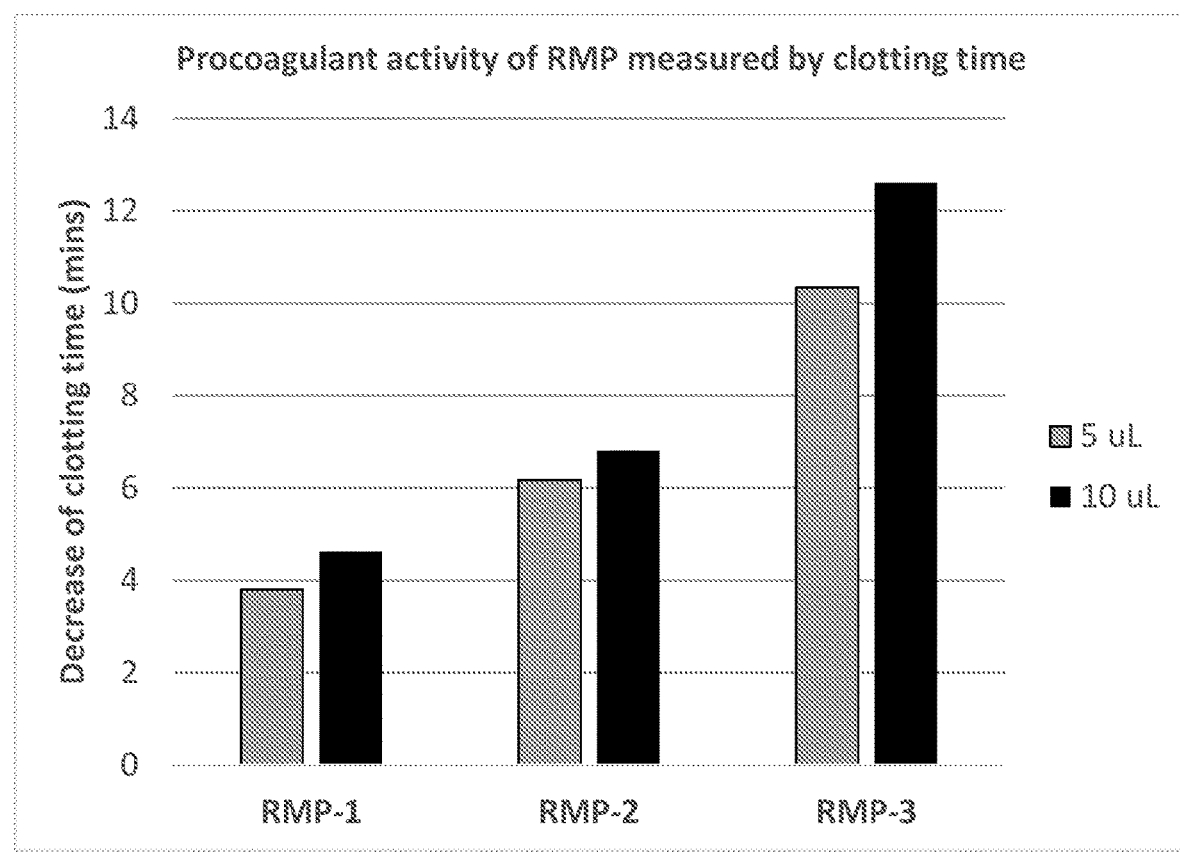
FIG. 2 is a bar graph comparing clotting time shortening (minutes; y-axis) mediated by 5 µM (left bar) or 10 µM (right bar) of RMP-1, RMP-2, and RMP-3 described in the Examples.
Figure 3:
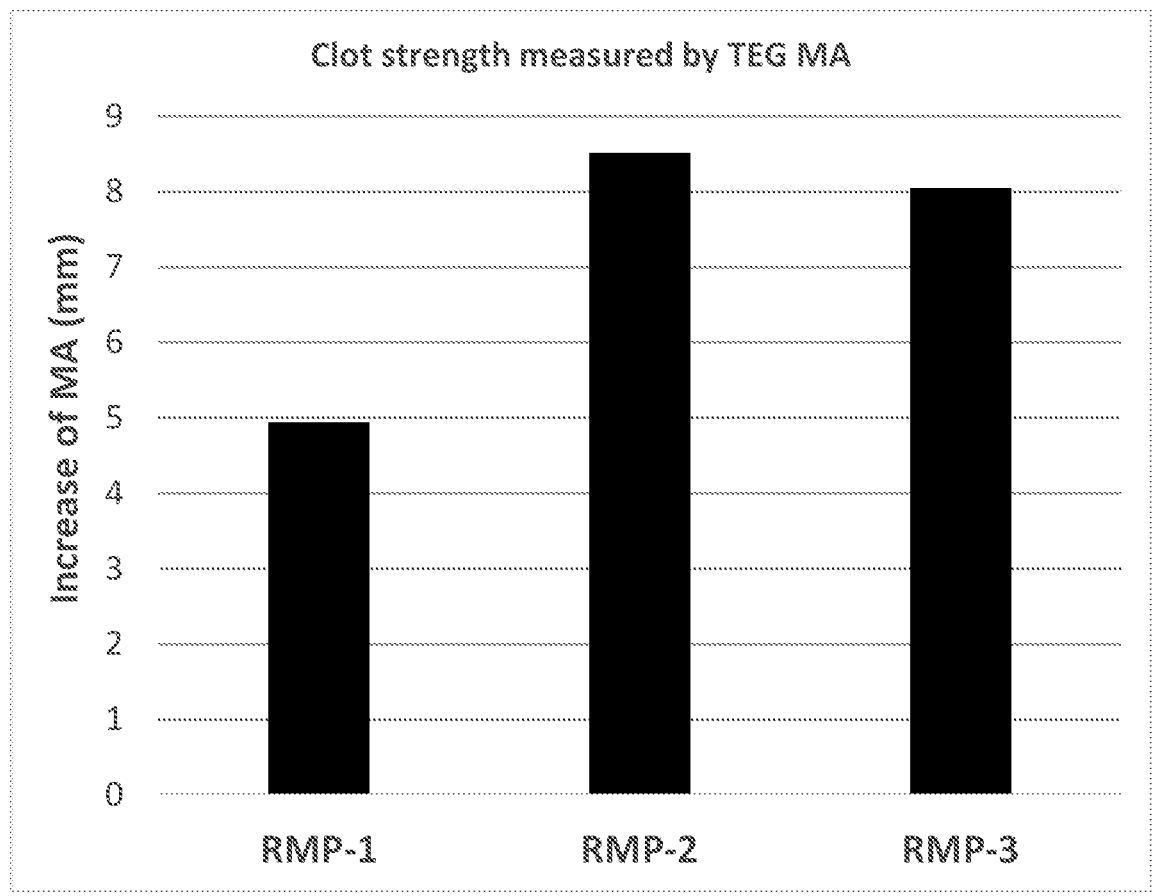
FIG. 3 is a bar graph comparing clot strength (Increase of TEG MA; y-axis) mediated by RMP-1, RMP-2, and RMP-3 described in the Examples.
Figure 4:
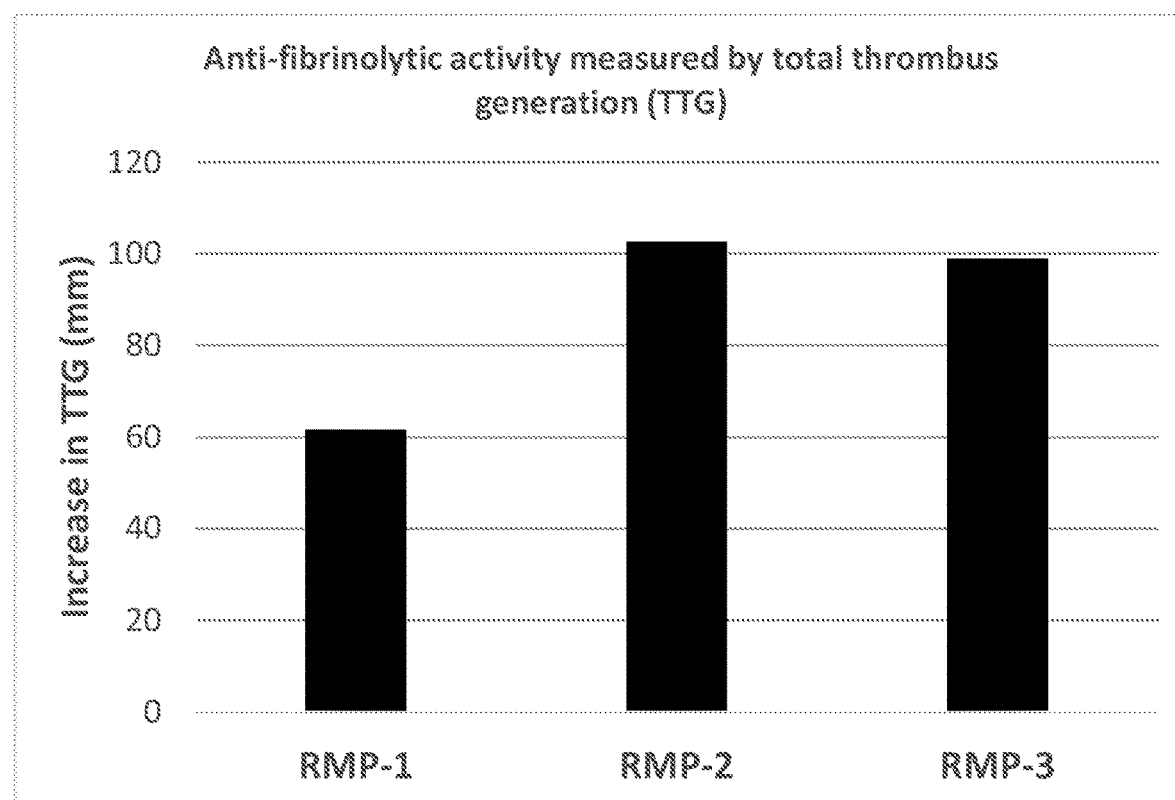
FIG. 4 is a bar graph comparing the anti-tPA-mediated fibrinolysis (increase of TG from control (mm/min); y-axis) induced by RMP-1, RMP-2, and RMP-3 described in the Examples.

Provided herein are improved compositions of red blood cell-derived microparticles (RMPs) and methods of use for reducing bleeding in a subject. RMPs have many advantages as hemostatic agents, including (but not limited to) ease and economy of production and minimal immunogenicity. Red blood cells (RBCs) are the most abundant type of blood cells, assuring an essentially unlimited and economical source for RMP production. RMP have an indefinite shelf-life with room temperature storage and do not require storage in blood banks, making them particularly advantageous for emergency situations. Additionally, RMP produced from type O Rh negative red cells (universal RMP) can be administered immediately without cross-matching.

The disclosure is based, at least in part, on the surprising identification of a subpopulation of RMPs with characteristics that are particularly advantageous for therapeutic applications. The particular subpopulation displaying the characteristics described herein is novel and provides technical advantages over previously described populations of RMPs in terms of, e.g., efficacy and reduced toxicity. RBC degradation products, including RMPs, have been linked to proinflammatory responses, toxicity, and severe side effects. See, e.g., Danesh et al., Blood. 2014; 123(5):687-696; and Zwicker et al., Br J Haematol. 2013; 160(4): 530-537. Indeed, elevated MP have been implicated in a variety of thrombophilic conditions such as sickle-cell disease (Camus et al., Blood. 2012; 120(25):5050) and thrombotic thrombocytopenia (TTP) (Galli et al., Thromb Haemost 1996. 75(3):427-31), and implicated in toxic events following blood transfusions (Donadee et al., Circulation 2011; 124: 465-476). Previously described RMP compositions carried a risk of adverse events. Remarkably, the subpopulation of RMPs described herein efficiently reduce bleeding while significantly minimizing toxicity and adverse side effects.

The disclosure herein describes various aspects of the subpopulation of RMPs provided in the composition. Compositions comprising RMPs displaying any one, any combination, or all of the features described herein are contemplated and encompassed by the invention.

In one aspect, the disclosure provides a composition comprising red cell-derived RMPs demonstrating significantly reduced acetylcholine esterase (AchE) activity. The reduction in AchE activity correlates with reduced toxicity of the RMPs in vivo. In various embodiments, the RMPs in the composition demonstrate an AchE activity of less than 20,000 pmol/min/$10^6$ particles (e.g., between 20,000 pmol/min/$10^6$ particles and 50 pmol/min/$10^6$ particles, wherein 50 pmol/min/$10^6$ particles or 25 pmol/min/$10^6$ particles is an optional lower limit for any of the ranges described herein). In preferred embodiments, the RMPs demonstrate an AchE activity of less than 10,000 pmol/min/$10^6$ particles, less than 5,000 pmol/min/$10^6$ particles, less than 2,500 pmol/min/$10^6$ particles, less than 1,000 pmol/min/$10^6$ particles, less than 500 pmol/min/$10^6$ particles, less than 350 pmol/min/$10^6$ particles, less than 250 pmol/min/$10^6$ particles, less than 200 pmol/min/$10^6$ particles, or less than 150 pmol/min/$10^6$ particles. In an exemplary aspect, the RMPs demonstrate an AchE activity of less than 350 pmol/min/$10^6$ particles. Methods of detecting AchE activity are known in the art (see, e.g., Ellman et al., Biochemical Pharmacology 1961; 7(2):88-95; Xie et al., J. Biol. Chem. 2007; 282:11765-11775; Wolkmer et al., Experimental Parasitology 2014; 132(4):546-549) and described in the Example provided herein.

Alternatively or in addition, the RMPs comprise a significantly reduced level of lipid rafts or components thereof compared to previously described RMP populations. Lipid rafts, also called "detergent-resistant membranes" (DRM), are membrane micro-domains rich in cholesterol and sphingolipids. Essentially all natural cell-derived microparticles (MP) consist mainly of lipid rafts. Remarkably, the composition of the instant disclosure, in various embodiments, comprises less lipid raft content (which is not limited to intact lipid rafts, but includes components of lipid rafts) than previously achieved. Merely for convenience in description this aspect of the disclosure, the lipid raft content of the RMPs may be compared to the lipid raft content of whole (i.e., non-fragmented) red blood cells. In various aspects, the lipid raft content of the RMPs of the composition is 10% or less (e.g., 5% or less, 3% or less, 2% or less, 1% or less, 0.5% or less (such as 0.1% or 0.05%)) that of the lipid content of whole red blood cells. While not wishing to be bound by any particular theory, AchE can serve as surrogate measure of lipid rafts, as the protein is anchored in cell membranes by a transmembrane protein PRiMA (proline-rich membrane anchor) and is integrated in lipid raft micro-domains. See, e.g., Xie at al., J. Biol. Chem. 2010; 285(15): 11537-11546, which also provides materials and methods for determining the lipid raft content in a biological sample. Alternative markers of lipid raft include, but are not limited to, stomatin, flotillin, and caveolae. Lipid rafts also may be characterized using proteomics methods. See, e.g., Foster and Chan, Subcell Biochem. 2007; 43:35-47.

Alternatively or in addition, 20%-50% of the RMPs in the composition display phosphatidylserine. For example, optionally, 30%-45% of the RMPs in the composition display phosphatidylserine. In this regard, the composition provides a subpopulation of RMPs with an optimal level of phosphatidylserine activity to promote hemostasis (e.g., promote coagulation, reduce bleeding) while minimizing thrombogenic potential. Phosphatidylserine can be measured in a variety of ways. For example, a surrogate measure of phosphatidylserine includes detecting Annexin V binding via flow cytometry. See, e.g., Koopman et al., "Annexin V for flow cytometric detection of phosphatidylserine expression on B cells undergoing apoptosis". Blood 1994; 84(5): 1415-20. In one exemplary method, the ratio of Annexin V binding+ to CD235a+ (a general marker of RMPs) cells is determined. In various aspects, the ratio of AnV+/CD235a+ is 0.2-0.5, such as 0.3-0.4.

Optionally, the internal density of the RMPs of the composition is less than 3.5% of the internal density of intact red blood cells. In some aspects, the RMPs have an internal density of about 0.1%-3.5% (e.g., about 0.5%-3%, about 0.5%-2.5%, or about 1%-2%) of the internal density of whole red blood cells. Internal density of RMPs can be determined using a variety of techniques including, but not limited to, flow cytometry side scatter signal, as described herein. While not wishing to be bound by any particular theory, the reduce internal density is believed to be associated with reduced hemoglobin content. Free hemoglobin can be toxic in vivo, leading to, e.g., kidney failure. See, e.g., Gladwin et al., J Clin Invest. 2012; 122(4):1205-1208. The RMPs of the composition of the disclosure demonstrate reduced toxicity.

In various embodiments, the composition shortens time to initial clot formation as measured by thromboelastography (TEG) in whole blood and plasma. In this regard, the composition optionally shortens time to initial clot formation, as measured by thromboelastography, by at least two minutes (e.g., by at least three minutes or by at least four minutes). In various embodiments, the composition shortens time to initial clot formation as measured by thromboelastography (TEG) in whole blood and plasma by about two to about five minutes. Indeed, in various embodiments, the composition restores normal clotting, as indicated by shorter clot time, more rapid clot formation, or more stable clot development, as measured by TEG or rotational thromboelastometry (ROTEM) in whole blood and plasma.

Alternatively or in addition, the RMPs in the composition display a mean diameter of about 0.40-0.70 μm, such as about 0.40-0.60 μm or about 0.40-0.50 μm. Optionally, the mean diameter of the RMPs is about 0.45-0.50 μm. RMP size can be determined using any of a variety of routine laboratory techniques, including the methods described in the Example.

RMPs are degradation products of RBCs. The RMPs may be produced from fresh RBCs (i.e., RBCs isolated from blood samples within 24 hours of RMP production) or stored RBCs. In this regard, the RBCs are optionally frozen prior to production of the RMPs. For example, in various aspects, the RBCs have been frozen for up to one month, up to two months, up to three months, up to four months, or longer. RMPs can be generated using any of a number of techniques to disrupt red blood cell membranes, including sonication, centrifugation, heating, and treatment with ionophores. In various embodiments, the RMPs are produced by forcing red blood cells through an aperture to produce ruptured red blood cells, and further fragmenting the ruptured red blood cells by bombardment on a solid surface. The shear stress created by forcing the RBCs through an aperture at a pressure of, e.g., at least 25,000 psi (such as a pressure of about 35,000 psi) shears the RBCs, and the subsequence bombardment step further fragments the RBCs to produce a population of RMPs with the characteristic(s) described herein. The RMP in the composition can be fresh (i.e., prepared from RBCs within 24 hours of administration to a subject) or stored. Since RMPs have extended shelf-life, the composition may be stored for extended periods of time. RMP produced from expired blood are as effective as RMP from very fresh blood; thus, the disclosure provides a means for utilizing blood donations that may otherwise be unsuitable for clinical use.

Also provided is a method for treating excessive bleeding in the subject. The method comprises administering to the subject the composition comprising RMPs described herein. For example, the method comprises administering a composition comprising RMPs demonstrating acetylcholine esterase (AchE) activity of less than 350 pmol/min/$10^6$ particles and/or having mean diameter of about 0.40-0.6 μm and/or wherein 20%-50% of the RMPs in the composition display phosphatidylserine and/or wherein the composition shortens time to initial clot formation as measured by thromboelastography (TEG) in whole blood and plasma (e.g., by at least two minutes).

As used herein, "treating" and "treatment" refers to any reduction in bleeding in a subject. "Treating" and "treatment" includes therapeutic and prophylactic measures. One of ordinary skill in the art will appreciate that any degree of protection from, or amelioration of, excessive bleeding is beneficial to a subject, such as a human patient. Accordingly, the method in one aspect is performed as soon as possible after it has been determined that a subject is at risk for abnormal blood loss (e.g., prior to surgery in a subject suffering from or at risk of suffering from a coagulation or platelet disorder) or as soon as possible after a bleeding episode occurs.

Excessive bleeding may be caused by a variety of disorders or conditions, and may be congenital or acquired (e.g., prompted by other therapeutic agents). The subject may suffer from (i.e., the excessive bleeding is caused by), e.g., a platelet disorder or a coagulation disorder. Coagulation disorders include bleeding disorders caused by deficient blood coagulation factor activity. Blood coagulation factors include, but are not limited to, Factor V (FV), FVII, FVIII, FIX, FX, FXI, FXIII, FII (responsible for hypoprothrombinemia), and von Willebrand's factor. The subject may suffer from chronic liver disease. Platelet disorders are caused by deficient platelet function or abnormally low platelet number in circulation. Low platelet count may be due to, for instance, underproduction, platelet sequestration, or uncontrolled patent destruction. Thrombocytopenia (platelet deficiencies) may be present for various reasons, including chemotherapy and other drug therapy, radiation therapy, surgery, accidental blood loss, and other disease conditions. For example, the thrombocytopenia is optionally associated with bone marrow failure, aplastic anemia, myelodysplastic syndrome, or leukemia. Platelet disorders also include, but are not limited to, Von Willebrand Disease, paraneoplastic platelet dysfunction, Glanzman's thrombasthenia, and Bernard-Soulier disease. Excessive bleeding also may be caused by hemorrhagic conditions induced by trauma; a deficiency in one or more contact factors, such as FXI, FXII, prekallikrein, and high molecular weight kininogen (HMWK); vitamin K deficiency; a fibrinogen disorder, including afibrinogenemia, hypofibrinogenemia, and dysfibrinogenemia; and alpha2-antiplasmin deficiency. In various embodiments, the excessive bleeding is caused by surgery, trauma, intracerebral hemorrhage, liver disease, renal disease, thrombocytopenia, platelet dysfunction, hematomas, internal hemorrhage, hemarthroses, hypothermia, menstruation, pregnancy, and Dengue hemorrhagic fever.

Optionally, the excessive bleeding is caused by drug treatment. For example, in various embodiments, the excessive bleeding is caused by an anticoagulant, such as blood thinners such as Coumadin (warfarin, which is also a vitamin K antagonist), heparin (e.g., low molecular weight heparin, such as enoxaparin or dalteparin), an inhibitor of prothrombinase complex (e.g., fondaparinux or rivaroxaban), an inhibitor of FXa (e.g., apixaban (Eliquis)), or an inhibitor of thrombin (e.g., dabigatran). The excessive bleeding also may be caused by aspirin (which inhibits platelet function and can result in serious bleeding, especially in combination with other disorders or medications), clopidogrel (PLAVIX), and the like. These anticoagulants do not have antidotes, and hemorrhagic complications stemming from these anticoagulants are dangerous to patients. The composition of the disclosure is effective in treating and/or preventing excessive bleeding in these contexts.

In various embodiments, the subject is undergoing therapy with a blood thinner (or blood thinner treatment has been discontinued within a period of time such that the biological effects of the blood thinner remain). One advantage of the composition of the invention is that RMPs of the instant composition correct hemostatic defects induced by blood thinners, even when blood thinners are present. The composition of the disclosure demonstrates universal hemostatic activity and, as such, is suitable for treating bleeding in patients that suffer from multiple hemostatic defects.

The composition (e.g., pharmaceutical composition) is formulated with a physiologically-acceptable (i.e., pharmacologically-acceptable) carrier, buffer, excipient, or diluent. The particular carrier employed is limited only by chemico-physical considerations, such as solubility and lack of reactivity with the RMPs, and by the route of administration. Physiologically-acceptable carriers are well known in the art. Illustrative pharmaceutical forms suitable for injectable use include without limitation sterile aqueous solutions or dispersions. Injectable formulations are further described in, e.g., Pharmaceutics and Pharmacy Practice, J. B. Lippincott Co., Philadelphia. Pa., Banker and Chalmers. eds., pages 238-250 (1982), and ASHP Handbook on Injectable Drugs, Toissel, 4th ed., pages 622-630 (1986)). A pharmaceutical composition comprising RMPs provided herein is optionally placed within containers, along with packaging material that provides instructions regarding the use of such pharmaceutical compositions. Generally, such instructions include a tangible expression describing the reagent concentration, as well as, in certain embodiments, relative amounts of excipient ingredients or diluents that may be necessary to dilute the pharmaceutical composition.

If desired, the composition comprises one or more additional pharmaceutically-effective agents. Alternatively or in addition, the composition is provided as a therapeutic regimen including administration of other pharmaceutically-effective agents (concurrently or separated by time). The composition may be administered in combination with other substances and/or other therapeutic modalities to achieve an additional or augmented biological effect. Co-treatments include, but are not limited to, plasma-derived or recombinant coagulation factors, hemophilia prophylaxis treatments, immunosuppressants, plasma factor-inhibiting antibody antagonists (i.e., anti-inhibitors), antifibrinolytics, antibiotics, hormone therapy, anti-inflammatory agents (e.g., Non-Steroidal Anti-Inflammatory Drugs (NSAIDs) or steroidal anti-inflammatory substances), procoagulants, blood thinner, and pain relievers. In one aspect, administration of the composition allows a reduction in the dose of co-therapeutic required to achieve a desired biological response.

The invention thus includes administering to a subject the composition of the disclosure in combination with one or more additionally suitable substances(s), each being administered according to a regimen suitable for that medicament. Administration strategies include concurrent administration (i.e., substantially simultaneous administration) and non-concurrent administration (i.e., administration at different times, in any order, whether overlapping or not) of the RMP composition and one or more additionally suitable agents(s). It will be appreciated that different components are optionally administered in the same or in separate compositions, and by the same or different routes of administration.

A particular administration regimen for a particular subject will depend, in part, upon the amount of composition administered, the route of administration, the particular ailment being treated, considerations relevant to the recipient, and the cause and extent of any side effects. The amount of composition administered to a subject (e.g., a mammal, such as a human) and the conditions of administration (e.g., timing of administration, route of administration, dosage regimen) are sufficient to affect the desired biological response over a reasonable time frame. Purely by way of illustration, in one aspect, the method comprises administering, e.g., from about $1 \times 10^{10}$ RMPs/kg to about $3 \times 10^{11}$ RMPs/kg to a subject (e.g., about $5 \times 10^{10}$ RMPs/kg to about $2 \times 10^{11}$ RMPs/kg).

The method comprises, in various aspects, administration of the composition to treat an acute condition (e.g., bleeding caused by surgery or trauma) for a relatively short treatment period, e.g., one to 14 days. It is also contemplated that the composition may be administered over a longer treatment course (e.g., lasting weeks or months) should the nature of the patient's condition require prolonged treatment. The method in various embodiments comprises multiple administrations of composition to a subject (e.g., once a day, twice a day, three times per day, four times per day, or more).

Suitable methods of administering a physiologically-acceptable composition, such as a composition comprising RMPs as described herein, are well known in the art. Although more than one route can be used to administer a composition, a particular route can provide a more immediate and more effective reaction than another route. In one aspect, the composition of the disclosure is administered intravenously, intraarterially, or intraperitoneally to introduce RMPs into circulation. Non-intravenous administration also is appropriate, particularly with respect to low molecular weight therapeutics. In certain circumstances, it is desirable to deliver a pharmaceutical composition comprising RMPs as described herein vaginally, rectally, pulmonary; through injection by intracerebral (intra-parenchymal), intracerebroventricular, intramuscular, intra-ocular, intra-portal, intralesional, intramedullary, intrathecal, intraventricular, transdermal, subcutaneous, intranasal, urethral, or enteral means; by sustained release systems; or by implantation devices. If desired, the composition is administered regionally via intraarterial or intravenous administration feeding a region of interest, e.g., via the femoral artery for delivery to the leg. Where an implantation device is used, the device in one aspect is implanted into any suitable tissue, and delivery of the composition is in various aspects via diffusion, timed-release bolus, or continuous administration. In other aspects, the composition is administered directly to exposed tissue during surgical procedures or treatment of injury, or is administered via transfusion of blood procedures.

In view of the above, the invention provides the composition described herein for use in a method for the treatment of a subject, such as a method for the treatment of a disorder where RMPs are beneficial. In one aspect, the disclosure provides the composition described herein for use in treating excessive bleeding or blood loss in a subject in need thereof. The method comprises administering to the subject the composition of the invention in an amount and under conditions effective to treat or prevent, in whole or in part, excessive blood loss. The invention further provides RMPs having one or more (or all) of the characteristics described herein for use in the manufacture of a medicament. For example, the RMPs can be used in the manufacture of a medicament (e.g., a composition) for the treatment of excessive bleeding or blood loss in a subject in need thereof.

EXAMPLES

Cell derived microparticles (MP), are small vesicle (<1 um) released in cell activation or apoptosis. Depending on stimulus, MPs can be heterogeneous in phenotype and functional activities such as hemostatic vs thrombogenic vs proinflammatory. In this study, three populations of RMPs were produced, which displayed different combinations of structural and functional characteristics. Characteristics studied include PCA (proxy of hemostatic activity), acetylcholine esterase (AchE) activity, and toxicity.

A subpopulation of RMPs was identified which demonstrated particularly advantageous characteristics linked with improved efficacy and reduced toxicity which plagues other RMP compositions.

One population of RMPs was produced by forcing RBCs through an aperture (35,000 psi) three times (using Constant System Cell Disruptor) to produce ruptured red blood cells, and further fragmenting the ruptured red blood cells by bombardment on a solid surface (RMP-1). The resulting RMP were washed and collected by centrifugation. A second population of RMPs was produced by calcium ionophore treatment of RBCs (RMP-2). Supernatants of fresh RBC exposed to Ca2+/ionophore (A23187) (10 μM) for 30 minutes were centrifuged to collect RMPs. A third population was released from packed cells (PC) following storage up to 42 days (RMP-3); RBCs were taken from stored PC at intervals up to 42 days (stored at 4° C.), then centrifuged to recover RMP.

Flow cytometric counts were by CD235a (glycophorin A) and annexinV (AnV) binding. CD235a labeling of RMP was performed by addition of 20 μL of RMP sample to 4 μL of fluorescence-labeled mAb and incubation for 20 min at room temperature with orbital shaking. The mixtures were then diluted with 1000 μL of cold HEPES/saline (pH 7.4), and kept on ice until ready for flow cytometry. For marker annexin V, 20 μL of RMP sample was incubated with 3 μL of 0.2 M $CaCl_2$ solution plus 2 μL of annexin V-FITC (10 μg/mL) for 20 min, then 500 μL of HEPES/saline, then processed as above. The samples then were assayed for MP on a Beckman Coulter FC-500 flow cytometer, calibrated by Megamix beads to set appropriate amplifying voltage for FS, SS, FL1, and FL2 and suitable gating for MP. Run time was 30 seconds and flow rate was calibrated as previously described (Jy et al., Thromb Haemost. 2013;110(4):751-60). Event counting was triggered by fluorescent signal (FL1 or FL2) rather than by forward scatter (FS), giving improved detection efficiency. The MP gate was set for size <1 um. Non-specific binding of mAb was assessed by fluorescence-labeled isotypic IgG.

Functional tests included Thrombo-elastography (TEG); equal counts of each sample type were compared, based on CD235a, and diluted as needed with particle-free pooled plasma (PFP). TEG measures clotting development by monitoring the increasing torque transmitted to a central pin dipping into the sample cup; the cup oscillates periodically through +/−4.5°. Parameters recorded for the present study were: R (lag to fibrin formation), MA (maximum amplitude, reflecting platelet function), and TTG (total thrombus generation). For each test, 330 μL of PFP were mixed with 5 or 10 µL of RMP ($2 \times 10^9$ particles/mL) for 5 min, then 20 µL of calcium (100 mM) was added to initiate the coagulation.

Acetylcholine esterase (AchE) activity, a marker on the red cell plasma membrane lipid rafts, was assayed by a colorimetric method (an adapted version of Ellman's AChE assay). The RMP was diluted using phosphate buffer (pH 7.5, 0.1M). 10.6 µL of 0.01M DTNB and 10.6 µL of 12.5 mM acetylthiocholine iodide was added and mixed with 150 µL of the diluted RMP. The samples were read at 405 nm at 1 min, 3 min, and 6 min intervals.

Toxicity of RMP was evaluated in male New Zealand White rabbits (mean 3.8 kg) and male Sprague Dawley rats (mean 280 g). All were anesthetized with 2% isoflurane. The femoral artery and vein were cannulated, and maintenance saline was administered at 3 mL/hr. The RMP samples were infused via cannulated femoral vein, and blood was collected via cannulated femoral artery at different time intervals. Vital signs including blood pressure, heart rate, respiratory rate, blood $O_2$ and $CO_2$ levels were continuously monitored. Some animals were sacrificed 4 hours after RMP injection to obtain the major organs for pathological examination. Some animals were sutured and returned to animal care facility for long term follow-up. Their behavior, mobility, food and water intake, body temperature, etc. were monitored daily for the first week, then weekly for the remaining 5 weeks.

RMP-1 was associated with the highest yield of therapeutic product, followed by RMP-2, which produced about 3× more therapeutic product than RMP-3.

AnV binding was expressed as ratio AnV+/CD235+, and is a marker of procoagulant phospholipid. This ratio was least in RMP-1 (0.28), followed by RMP-2 (0.48) and RMP-3 (0.98).

Procoagulant activity was estimated using TEG. The clotting time (R-time) showed greatest shortening with RMP-3 (10.2 min), followed by RMP-2 (6.7 min), and RMP-1 (3.6 min).

Anti-fibrinolytic activity was tested in the presence of 0.4 µg/mL of tissue plasminogen activator (tPA). All three species of RMP effectively inhibited t-PA-mediated fibrinolysis measured by TEG parameters, including MA, Ly30, and TTG (total thrombus formation). RMP-3 was most effective followed by RMP-2, and RMP-1.

Administration of RMP-1 to rabbits and rats at dosages from $1 \times 10^{10}$ to $1.2 \times 10^{12}$ RMP/kg did not cause any adverse events within six weeks of post-administration observation. Vital signs including heart rate, blood pressure, respiratory rate, blood oxygen levels, and body temperature remained normal during one hour post-RMP infusion. Long-term follow-up (6 weeks) showed normal behavior, appetite, and mobility. At highest dosage ($1.2 \times 10^{12}$ RMP/kg), all rats tested remained alive and gaining weight during and at the end of the six week observation period. At these dosages, the bleeding time was substantially shortened and total blood loss was reduced, in three different animal bleeding models.

A summary of the characteristics of the various RMP subpopulations described herein are set forth in Table 1. The first row is the RMP yield per mL of PC. The second row is the ratio between the RMP count detected by anti-glycophorin (CD235a) and the RMP count detected by Annexin V binding in the flow cytometer. The third row is the size of the RMP, calculated from forward scatters of the flow cytometric assay calibrated with three different sizes of beads. The last row is the percent of interior density of the RMP to the RBC, calculated from the side scatters (SS) of flow cytometric assay. All values are Mean±SEM.

TABLE 1

PROPERTIES OF RMP POPULATIONS

| Characteristics | RMP-1 (n = 10) | RMP-2 (n = 2) | RMP-3 (Week 6) (n = 10) | p-value |
|---|---|---|---|---|
| Yield ($\times 10^7$ RMP/mL RBC) | 1525 ± 64 | 325 ± 15 | 4.4 ± 0.6 | 1 vs. 2: 0.014<br>1 vs. 3: <0.001<br>2 vs. 3: 0.030 |
| Ratio (Annexin $V^+$ MP:CD235a$^+$ MP) | 0.28 ± 0.03 | 0.48 ± 0.05 | 0.99 ± 0.02 (n = 20) | 1 vs. 2: 0.0016<br>1 vs. 3: <0.001<br>2 vs. 3: <0.001 |
| Mean diameter (µm) | 0.42 ± 0.009 | 0.45 ± 0.003 | 0.57 ± 0.001 | 1 vs. 2: NS<br>1 vs. 3: <0.001<br>2 vs. 3: <0.001 |
| % Interior Density to RBC | 1.5 ± 0.07 | 4.8 ± 0.03 | 10.3 ± 0.52 | 1 vs. 2: <0.001<br>1 vs. 3: <0.001<br>2 vs. 3: 0.039 |

Size (mean diameter) of RMP detected by forward scatter (FS) was 0.57 µm in RMP-3. The value was somewhat larger than RMP-1 (0.42 µm) and RMP-2 (0.45 µm). The percent internal density of RMP to RBC measured by side scatter were lowest in RMP-1 (1.5%), followed by RMP-2 (4.8%), and RMP-3 (10.3%).

Acetylcholinesterase (AChE) activity was by far highest in RMP-3 (15,643 pmoles/min, per $10^6$ particles) versus 3,362 pmoles/min, per $10^6$ particles for RMP-2, and 149 pmoles/min, per $10^6$ particles for RMP-3. Presenting the data in an alternative way, AChE activity was lowest in RMP-1 (149 pmoles/min, per $10^6$ particles), which is 22- and 104-fold lower than that of RMP-2 (3,362 pmoles/min, per $10^6$ particles) and RMP-3 (15,643 pmoles/min, per $10^6$ particles), respectively.

The results herein demonstrate the advantages of a unique type of RMP characterized herein. This type of RMP exhibits distinctive surface characteristics and functional activities. The results demonstrate clear and decisive differences in functional, phenotypic, and toxicological properties of the three species compared. RMP-2 and RMP-3 are larger in size, higher in AnnV binding, and AChE expression compared to RMP-1. RMP-2 and RMP-3 demonstrated higher procoagulant activity than RMP-1, but RMP-1 demonstrated procoagulant activity; activity of RMP-2 and RMP-3 were higher in this regard. RMP-1 were associated with higher numbers of therapeutic product generated per mL of packed RBC.

Of all the parameters compared, the most striking difference among these three species of RMP is the AchE activity.

AchE activity of RMP-1 is about 25- and 150-fold lower than that RMP-2 and RMP-3, respectively. AchE is believed to be covalently linked to lipid rafts and, as such, serves as a surrogate marker of lipid rafts. Based on the AchE data, RMP-3 are practically devoid of lipid rafts, which are composed of many proinflammatory mediators such as adhesins and ligands for cell activation, proinflammatory lipids and cytokines, complements, immune complexes etc.

Prior to the disclosure, it was believed that hemostatic efficacy and toxicity were inseparably linked. The results described above demonstrate that the unique type of RMP identified herein surprisingly demonstrate no discernible toxicity, yet retain robust hemostatic efficacy.

The characteristics of RMP produced from previously frozen RBCs also was explored. Leuko-reduced, O+ packed RBCs were purchased from OneBlood.org. Each bag of packed RBCs were divided into four equal parts (70-75 mL). One part of the RBCs was stored at 4° C. and was used to produce RMPs within seven days after receiving the shipment. The remaining three parts were frozen at −20° C. and were thawed at 1, 2, or 3 months following initial freeze to produce RMPs. RMPs were produced by high pressure extrusion, as described herein, using a Constant System Cell Disruptor at 35,000 psi internal pressure. The RMP count (yield) was measured by flow cytometry using PE-labeled anti-glycophorin A monoclonal antibody as a marker. The procogulant activity of RMP was determined by thromboelastogram (TEG). As shown in Table 2, the resulting compositions of RMPs produced from unfrozen and frozen RBCs were not significantly different in terms of yield, procoagulant activity, and Annexin V binding. Use of previously frozen RBCs allows scaling up of production of RMPs.

TABLE 2

Production of RMP from Frozen vs. Unfrozen RBCs

| Source of RBC | RMP yields (counts/ml blood) | Procoagulant activity/ $7 \times 10^7$ RMP | Annexin V binding (% of total RMP) |
|---|---|---|---|
| Unfrozen RBC (Control) | $7.0 \times 10^9$ | 100% | 38% |
| RBC frozen for 1 month | $7.2 \times 10^9$ | 106% | 40% |
| RBC frozen for 2 months | $7.3 \times 10^9$ | 113% | 42% |
| RBC frozen for 3 months | $6.9 \times 10^9$ | 111% | 43% |

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the disclosure (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Throughout the specification, where formulations are described as including components or materials, it is contemplated that the formulations can also consist essentially of, or consist of, any combination of the recited components or materials, unless described otherwise. Likewise, where methods are described as including particular steps, it is contemplated that the methods can also consist essentially of, or consist of, any combination of the recited steps, unless described otherwise. The invention illustratively disclosed herein suitably may be practiced in the absence of any element or step which is not specifically disclosed herein. Moreover, any combination of the above-described elements in all possible variations thereof is encompassed by the disclosure unless otherwise indicated herein or otherwise clearly contradicted by context.

Recitation of ranges of values herein are merely intended to serve as a shorthand method of referring individually to each separate value falling within the range and each endpoint, unless otherwise indicated herein, and each separate value and endpoint is incorporated into the specification as if it were individually recited herein. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

What is claimed:

1. A composition comprising red cell-derived microparticles (RMPs) demonstrating acetylcholine esterase (AchE) activity of less than 350 pmol/min/$10^6$ particles/µL.

2. The composition of claim 1, wherein the RMPs demonstrate acetylcholine esterase (AchE) activity of less than 200 pmol/min/$10^6$ particles/µL.

3. The composition of claim 1, wherein 20%-50% of the RMPs in the composition display phosphatidylserine.

4. The composition of claim 3, wherein 30%-45% of the RMPs in the composition display phosphatidylserine.

5. The composition of claim 1, wherein the composition shortens time to initial clot formation as measured by thromboelastography (TEG) in whole blood and plasma by at least two minutes.

6. The composition of claim 1, wherein the mean diameter of the RMPs is about 0.40-0.6 µm.

7. The composition of claim 6, wherein the mean diameter of the RMPs is about 0.40-0.5 µm.

8. The composition of claim 7, wherein the mean diameter of the RMPs is about 0.47 µm.

9. The composition of claim 1, wherein the internal density of the RMPs is less than 3.5% of the internal density of whole red blood cells.

10. The composition of claim 9, wherein the internal density of the RMPs is about 0.5-3.0% of the internal density of whole red blood cells as measured by flow cytometry side scatter signal.

11. The composition of claim 1, wherein the RMPs are produced by forcing red blood cells through an aperture to produce ruptured red blood cells and further fragmenting the ruptured red blood cells by bombardment on a solid surface.

12. A method for treating excessive bleeding in the subject, the method comprising administering to the subject the composition of claim 1.

13. The method of claim 12, wherein the excessive bleeding is caused by thrombocytopenia or platelet dysfunction.

14. The method of claim 13, wherein the platelet dysfunction is caused by drug treatment.

15. The method of claim 12, wherein the excessive bleeding is caused by an anticoagulant.

16. The method of claim 15, wherein the anticoagulant is Coumadin, low molecular weight heparin, an inhibitor of prothrombinase complex, an inhibitor of FXa, or an inhibitor of thrombin.

* * * * *